United States Patent [19]

Rubinstein

[11] Patent Number: 5,229,423
[45] Date of Patent: Jul. 20, 1993

[54] USE OF BUTYLUREA AS A CONTRACEPTIVE AGENT

[75] Inventor: Arye Rubinstein, Monsey, N.Y.

[73] Assignee: Albert Einstein College of Medicine of Yeshiva University, Bronx, N.Y.

[21] Appl. No.: 847,193

[22] Filed: Mar. 6, 1992

[51] Int. Cl.$^5$ .............................................. A61K 31/17
[52] U.S. Cl. ...................................... 514/588; 514/843
[58] Field of Search ........................ 514/588, 843, 934

[56] References Cited

U.S. PATENT DOCUMENTS

| | | | |
|---|---|---|---|
| 3,813,695 | 6/1974 | Podell, Jr. et al. | 2/168 |
| 4,482,577 | 11/1984 | Goldstein et al. | 427/2 |
| 4,548,844 | 10/1985 | Podell et al. | 428/35 |
| 4,575,476 | 3/1986 | Podell et al. | 428/494 |
| 4,880,836 | 11/1989 | Elbaum | 514/588 |

OTHER PUBLICATIONS

Chemical Abstracts 81:68591w (Moyer), 1974.
Chemcial Abstracts 70:113223p (Lauro et al.), 1969.

*Primary Examiner*—Leonard Schenkman
*Attorney, Agent, or Firm*—Amster, Rothstein & Ebenstein

[57] ABSTRACT

This invention relates to the use of butylurea as a contraceptive agent. Butylurea may be used either alone or with a pharmaceutically acceptable carrier, and may be used in conjunction with conventional contraceptive means to abrogate sperm motility.

10 Claims, No Drawings

USE OF BUTYLUREA AS A CONTRACEPTIVE AGENT

FIELD OF THE INVENTION

This invention relates to the use of butylurea as a contraceptive agent. Specifically, it is directed to the use of butylurea as an agent for abrogating sperm motility.

BACKGROUND OF THE INVENTION

U.S. Pat. No. 4,880,836 describes the use of alkylureas as anti viral agents effective against Herpes I virus, Herpes II virus and the AIDS virus. This patent further describes methods of treating viral infection in media such as blood supply, blood bank and surfaces of all kinds by administering to such media an anti virally effective amount of alkylureas. The present invention describes the use of butylurea as a contraceptive agent.

It is an object of this invention to provide methods of abrogating sperm motility utilizing butylurea.

It is a further object of this invention to provide contraceptive compositions containing butylurea which compositions are useful in abrogating sperm motility, and methods of making such compositions.

It is another object of this invention to provide contraceptive compositions effective in abrogating sperm motility, which compositions may be used either alone or in conjunction with conventional contraceptive means and methods of making such compositions.

SUMMARY OF THE INVENTION

This invention is directed to the use of butylurea as a contraceptive agent, such contraceptive agent being capable of abrogating sperm motility. Butylurea may be used either alone or in conjunction with conventional contraceptive means as a contraceptive agent.

DETAILED DESCRIPTION OF THE INVENTION

This invention is directed to methods of abrogating sperm motility, contraceptive compositions which are useful in abrogating sperm motility and capable of enhancing the contraceptive capabilities of conventional contraceptive means, methods of making such contraceptive compositions, methods of enhancing the contraceptive capabilities of conventional contraceptive means and enhanced conventional contraceptive means.

Specifically, this invention is directed to the use of butylurea as a contraceptive agent capable of abrogating sperm motility.

The inventor has discovered that when sperm is put into contact with butylurea, the sperm's motility is abrogated. Hence, butylurea may be used as a contraceptive agent. Butylurea may be used in conjunction with pharmaceutically acceptable carriers to form contraceptive compositions which contraceptive compositions may be used alone as contraceptive agents, or in conjunction with a conventional contraceptive means.

For example, butylurea may be combined with a pharmaceutically acceptable carrier to form a contraceptive composition. Such pharmaceutically acceptable carrier may be a contraceptive or vaginal foam. In a preferred embodiment of this invention, butylurea is combined with a contraceptive or vaginal foam. The resulting contraceptive composition will have an enhanced ability to abrogate sperm motility.

Such contraceptive compositions, or butylurea alone, may be used to coat conventional contraceptive means, such as condoms, diaphragms or sponges. The coating of such conventional contraceptive means with either such contraceptive composition, or with butylurea alone, will result in enhanced conventional contraceptive means. The coating of the conventional contraceptive means with butylurea may be performed by priming the conventional contraceptive means using a priming treatment, such as flame, oxidizing acid, corona discharge or plasma, coating the primed means with a liquid solution of hydrogel polymer and absorbing the butylurea into the hydrogel polymer. Hydrogel polymer coating methods are discussed in U.S. Pat. Nos. 4,575,476, 4,499,154, and 4,482,577. The coating of conventional contraceptive means with butylurea, utilizing the hydrogel polymer coating method, will result in enhanced conventional contraceptive means with increased contraceptive capabilities. When sperm is put into contact with such coated contraceptive means, the motility of the sperm is abrogated. Hence, butylurea may be used as a contraceptive aqents.

In addition, butylurea may be an effective anti viral agent, and may be used to inhibit the transmission of HIV. Hence, if a contraceptive composition includes butylurea, that composition may be effective in both abrogating sperm motility and inhibiting the transmission of HIV.

EXAMPLE

Fresh sperm was obtained from four healthy volunteers. The level of sperm motility for each of the samples was recorded in a hemacount-chamber and scored as normal, reduced or absent.

Next, solutions of butylurea in phosphate buffered saline (PBS) at concentrations of 100 mMol, 15 mMol and 10 mMol were added to the sperm samples. The sperm was then tested 1 to 2 minutes, 15 minutes and 1 hour after incubation with the butylurea. The results are set out in Table I below:

TABLE I

| Donor | Sperm Motility | | |
|---|---|---|---|
| | After 1–2' | 15' | 1 hour |
| 1 | reduced | absent 45% | absent 100% |
| 2 | reduced | absent 45% | absent 100% |
| 3 | reduced | absent 45% | absent 100% |
| 4 | reduced | absent 45% | absent 100% |

After 1–2 minutes of incubation with the butylurea, the sperm motility of all four volunteers was reduced. After 15 minutes of incubation with butylurea, the sperm motility of all four individuals was reduced 45%. After 1 hour of incubation with butylurea, the sperm motility of all four volunteers was completely abrogated. This shows that butylurea is capable of completely abrogating sperm motility.

Although the invention herein has been described with reference to a particular embodiment, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method of abrogating sperm motility which comprises putting sperm into contact with butylurea either alone or in conjunction with a pharmaceutically acceptable carrier.

2. The method according to claim 1 wherein the pharmaceutically acceptable carrier is a contraceptive foam or a vaginal foam.

3. A method of enhancing the contraceptive capabilities of conventional contraceptive means which comprises coating a conventional contraceptive means with a contraceptive composition comprising butylurea either alone or in conjunction with a pharmaceutically acceptable carrier.

4. The method according to claim 3 wherein the pharmaceutically acceptable carrier is a contraceptive or a vaginal foam.

5. The method according to claim 3 wherein the conventional contraceptive means is selected from the group consisting of a condom, a diaphragm or a sponge.

6. The method according to claim 3 wherein the coating of the conventional contraceptive means is performed by priming the conventional contraceptive means with a conventional priming treatment, coating the primed conventional contraceptive means with a liquid solution of hydrogen polymer and absorbing the contraceptive composition into the hydrogen polymer.

7. An enhanced conventional contraceptive means which comprises a conventional contraceptive means coated with butylurea either alone or in conjunction with a pharmaceutically acceptable carrier.

8. The enhanced conventional contraceptive means according to claim 7 wherein the pharmaceutically acceptable carrier is a contraceptive or a vaginal foam.

9. The enhanced contraceptive means according to claim 7 wherein the conventional contraceptive means is selected from the group consisting of condom, a diaphragm or a sponge.

10. An enhanced conventional contraceptive means which comprises a contraceptive foam or a vaginal foam and butylurea.

* * * * *